United States Patent
Aladahalli et al.

(10) Patent No.: US 11,160,528 B2
(45) Date of Patent: Nov. 2, 2021

(54) SYSTEM AND METHOD FOR VISUALIZATION OF ULTRASOUND VOLUMES

(71) Applicant: General Electric Company, Schenectady, NY (US)

(72) Inventors: Chandan Kumar Mallappa Aladahalli, Bangalore (IN); Krishna Seetharam Shriram, Bangalore (IN); Vivek Prabhakar Vaidya, Bangalore (IN); Arathi Sreekumari, Bangalore (IN); Jiayu Chen, Palo Alto, CA (US); Hidenori Shikata, Sunnyvale, CA (US)

(73) Assignee: General Electric Company, Schenectady, NY (US)

( * ) Notice: Subject to any disclaimer, the term of this patent is extended or adjusted under 35 U.S.C. 154(b) by 905 days.

(21) Appl. No.: 15/372,688

(22) Filed: Dec. 8, 2016

(65) Prior Publication Data

US 2017/0172540 A1   Jun. 22, 2017

(30) Foreign Application Priority Data

Dec. 18, 2015 (IN) .......................... 6779/CHE/2015

(51) Int. Cl.
*A61B 8/08* (2006.01)
*A61B 8/00* (2006.01)

(52) U.S. Cl.
CPC ............ *A61B 8/0858* (2013.01); *A61B 8/085* (2013.01); *A61B 8/463* (2013.01); *A61B 8/5223* (2013.01); *A61B 8/56* (2013.01)

(58) Field of Classification Search
None
See application file for complete search history.

(56) References Cited

U.S. PATENT DOCUMENTS

| | | | | |
|---|---|---|---|---|
| 5,926,568 A * | 7/1999 | Chaney | ................. | G06K 9/6206 382/128 |
| 6,594,378 B1 * | 7/2003 | Li | .......................... | G06T 3/0068 128/922 |
| 7,545,979 B2 * | 6/2009 | Fidrich | ..................... | G06T 7/12 382/128 |

(Continued)

OTHER PUBLICATIONS

Didier et al., "A chest wall model based on rib kinematics". 2009 IEEE Second International Conference in Visualisation. pp. 159-164 (Year: 2009).*

(Continued)

*Primary Examiner* — Yi-Shan Yang

(57) ABSTRACT

A method for assisted reading of automated ultrasound image volumes includes receiving a plurality of scan images generated from an imaging device, wherein the plurality of scan images comprises a chest wall region. The method further includes determining a chest wall model representative of the chest wall region based on the plurality of scan images. The method also includes determining a plurality of segmented scan images segmented along the chest wall region based on the chest wall model. In addition, the method includes determining lesion information using an automated lesion detection technique applied to the plurality of segmented scan images. The method also includes displaying the plurality of scan images along with at least one of the lesion information and the chest wall model.

26 Claims, 6 Drawing Sheets

(56) References Cited

U.S. PATENT DOCUMENTS

| | | | | |
|---|---|---|---|---|
| 2007/0086640 | A1* | 4/2007 | Luo | G06K 9/38 |
| | | | | 382/132 |
| 2010/0303314 | A1* | 12/2010 | Chen | G06T 7/33 |
| | | | | 382/128 |
| 2011/0229005 | A1* | 9/2011 | Den Harder | G06K 9/3233 |
| | | | | 382/131 |
| 2012/0014578 | A1* | 1/2012 | Karssemeijer | G06T 7/0012 |
| | | | | 382/131 |
| 2014/0226884 | A1* | 8/2014 | Porikli | A61N 5/1037 |
| | | | | 382/131 |
| 2015/0087979 | A1* | 3/2015 | Zhang | A61B 8/4209 |
| | | | | 600/440 |
| 2015/0297099 | A1* | 10/2015 | Arad (Abboud) | A61B 5/686 |
| | | | | 600/375 |
| 2016/0005193 | A1* | 1/2016 | Markov | G06T 7/11 |
| | | | | 382/131 |
| 2016/0117818 | A1* | 4/2016 | Park | A61B 5/7425 |
| | | | | 382/131 |
| 2018/0350068 | A1* | 12/2018 | Kutra | G06T 7/50 |

OTHER PUBLICATIONS

Klinder et al., "Automated model-based rib cage segmentation and labeling in CT images". MICCAI 2007, Part II, LNCS 4792, pp. 195-202 (Year: 2007).*

* cited by examiner

SYSTEM AND METHOD FOR VISUALIZATION OF ULTRASOUND VOLUMES

BACKGROUND

Embodiments of the present specification relate generally to visualization of image volumes, and more particularly to systems and methods for assisted reading of automated ultrasound volumes.

Imaging modalities such as Computed Tomography (CT), Magnetic Resonance Imaging (MRI), and Ultrasound (US) are configurable to acquire image data sets corresponding to internal structures and tissues of a subject for medical diagnosis and treatment. In recent years, advanced visualizing technology has been used to view complex three-dimensional (3D) structures inside the subject that are otherwise difficult to study via standard slice images. For example, rendering of image volumes and time indexed data sets corresponding to the subject are widely used in medical diagnosis.

Further, while rendering an affected region in the subject, where the affected region includes a plurality of objects of interest, displaying surrounding tissues provides a positional relationship, thereby enhancing understanding of users (e.g., clinicians, medical practitioners, and the like) carrying out the medical diagnosis. For improved visualization, it is highly desirable that shapes of the plurality of objects of interest are clearly reproduced simultaneously in one image. Also, better visualization helps the users to effectively assess, diagnose and select treatment options. Moreover, enhanced rendering techniques also help patients in understanding the medical condition and providing informed consent for suggested medical procedures. Breast cancer is one of the leading causes of cancer related deaths in women across the world and early detection plays an important role in effective management of the disease. The use of ultrasound imaging as a breast cancer screening tool is increasing steadily due to relative cost advantage and patient comfort considerations. Also, ultrasound images may provide improved detection sensitivity in specific sections of populations such as young women with relatively dense breast tissue.

Known methods for detecting lesions in ultrasound images of the breast have some disadvantages. For example, scanning the patient with the ultrasound probe is highly operator dependent, which may result in inconsistent and inaccurate ultrasound scans. Moreover, relatively low quality of ultrasound images and the addition of artifacts such as speckle noise, shadows, ringing, and the like may increase the difficulty of lesion detection within ultrasound images.

Automated breast ultrasound (ABUS) scan volume are often acquired from various angles. However, utilizing the redundancy information in these volumes is a challenge. Also, the inclusion of the non-breast regions such as the ribs and chest wall confounds the detection of lesions both by the clinicians and computed assisted design (CAD) algorithms. Additionally, automated breast scan volumes are typically voluminous in nature and medical personnel require machine assistance in examining the data set.

BRIEF DESCRIPTION

In accordance with one aspect of present specification, a method is disclosed. The method includes receiving a plurality of scan images generated from an imaging device. The plurality of scan images comprises a chest wall region. The method further includes determining a chest wall model representative of the chest wall region based on the plurality of scan images. The method also includes determining a plurality of segmented scan images segmented along the chest wall region based on the chest wall model. In addition, the method includes determining lesion information using an automated lesion detection technique applied to the plurality of segmented scan images. The method also includes displaying the plurality of scan images along with at least one of the lesion information and the chest wall model.

In accordance with another aspect of the present specification, a system is disclosed. The system includes an imaging device configured to generate a plurality of scan images, wherein the plurality of scan images comprises a chest wall region. The system further includes a chest wall detector unit communicatively coupled to the imaging device and configured to generate a chest wall model based on the plurality of scan images. The system also includes a segmentation unit communicatively coupled to the chest wall detector unit and configured to segment the plurality of scan images along a boundary of the chest wall to determine a plurality of segmented scan images. The system further includes lesion detector unit communicatively coupled to the segmentation unit and configured to generate lesion information in the plurality of scan images. The system also includes a display unit communicatively coupled to the lesion detector unit and configured to display the plurality of scan images along with at least one of the lesion information and the chest wall model.

In accordance with another aspect of the present specification, a non-transitory computer readable medium having instructions is disclosed. The instructions enable at least one processor to receive a plurality of scan images generated from an imaging device, wherein the plurality of scan images comprises a chest wall region. The instructions further enable the at least one processor to determine a chest wall model representative of the chest wall region based on the plurality of scan images. The instructions further enables the at least one processor to determine a plurality of segmented scan images segmented along the chest wall region based on the chest wall model. The instructions also enable the at least one processor to determine lesion information using an automated lesion detection technique applied to the plurality of segmented scan images. In addition, the instructions enable the at least one processor to display the plurality of scan images along with at least one of the lesion information and the chest wall model.

DRAWINGS

These and other features and aspects of embodiments of the present invention will become better understood when the following detailed description is read with reference to the accompanying drawings in which like characters represent like parts throughout the drawings, wherein.

DETAILED DESCRIPTION

As will be described in detail hereinafter, systems and methods configured for visualization of ultrasound volumes are presented. More particularly, the systems and methods are configured for assisted reading of automated ultrasound volumes, such as breast ultrasound volumes.

Figure 1:
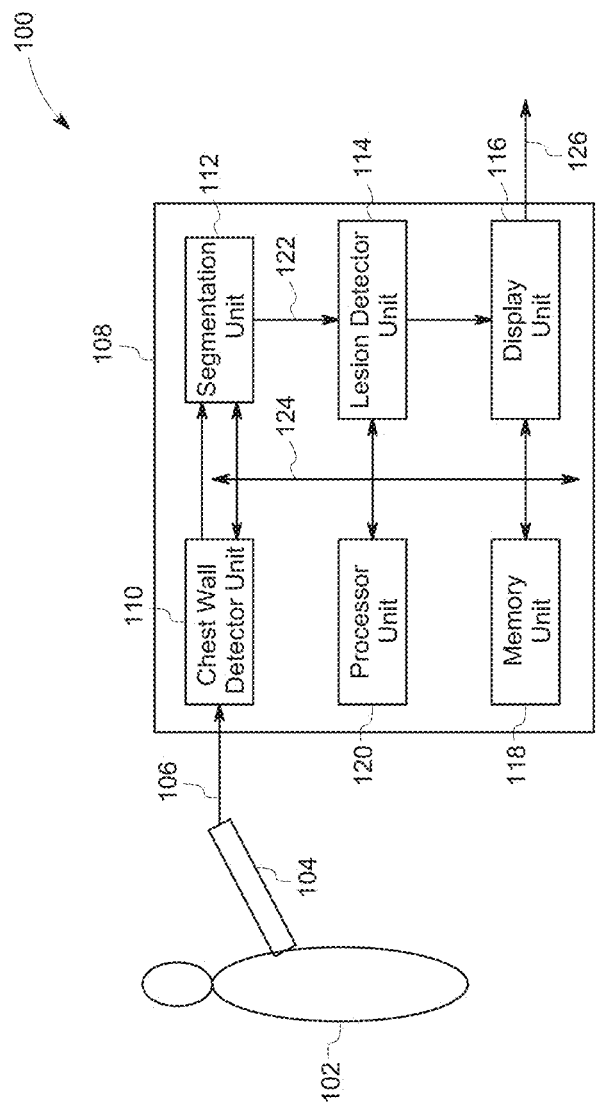
FIG. 1 is a diagrammatic illustration of a system for visualization of ultrasound volumes, in accordance with aspects of the present specification.

FIG. 1 is a diagrammatic illustration of an imaging system 100 having an enhanced visualization capability, in accordance with one aspect of the present specification. In one embodiment, the imaging system 100 is an ultrasound system, although other embodiments of imaging system include a magnetic resonance imaging (MRI) system and a computer tomography (CT) imaging system. The imaging system 100 includes an imaging device 104 such as ultrasound scanning device configured to acquire a plurality of image volumes 106 from a subject 102 during medical examination. In one embodiment, the plurality of image volumes includes a left scan volume corresponding to an image volume generated from scanning a left portion of the breast, a right scan volume corresponding to an image volume generated from scanning a right portion of the breast, and a center scan volume corresponding to an image volume generated from scanning the center portion of the breast. In this embodiment, the plurality of image volumes 106 corresponds to automated breast ultrasound (ABUS) image volumes.

The imaging system 100 further includes a visualization subsystem 108 communicatively coupled to the imaging device 104 and configured to receive the plurality of image volumes 106. The visualization subsystem 108 is further configured to process the plurality of image volumes 106 to generate additional information helpful for assisted reading of image volumes and provide a visualization output 126. In one embodiment, the visualization subsystem 108 is configured to determine at least one of a rib information, a chest wall information, and a lesion information based on the ABUS and render the information for assisting medical practitioners. In a presently contemplated configuration, the visualization subsystem 108 includes a chest wall detector unit 110, a segmentation unit 112, a lesion detector unit 114, a display unit 116, a memory unit 118, and a processor unit 120 communicatively coupled to each other through a communication bus 124.

The chest wall detector unit 110 is communicatively coupled to the imaging device 104 and configured to receive the plurality of image volumes 106. Each of the plurality of image volumes 106 includes a plurality of scan images. The plurality of scan images includes a chest wall region. The chest wall detector unit 110 is configured to determine a chest wall model representative of the chest wall region based on the plurality of scan images. In one embodiment, the plurality of scan images corresponding to one of the image volumes is processed. In one embodiment, the chest wall detector unit 110 is configured to identify ribs in the chest region based on the plurality of scan images. In another embodiment, the chest wall detector unit 110 is configured to determine a chest wall surface based on the plurality of scan images. In one embodiment, a rib centerline is extracted based on a recursive tracing technique. In another embodiment, the rib information is obtained using orientation space filtering. In yet another embodiment, a gradient ring feature map is obtained for determining the chest wall surface in the plurality of scan images.

In certain embodiments, the chest wall is detected based on a two-step registration technique. The two-step registration technique uses an atlas (or a template image) representative of a chest wall model. In the first step of the two-step registration technique, the atlas is initialized for registration with the plurality of scan images. In one embodiment, the atlas may be determined offline using a plurality of image volumes previously acquired and stored in the memory unit 118. The initialization of atlas includes a rough segmentation of one or more of the plurality of scan images and a rigid registration with the atlas. The deformations obtained from the registration are incorporated into the atlas to complete the initialization. In the second step, a deformable registration technique is used to align the atlas with one or more of the plurality of scan images. The deformable registration technique may include scaling and rotation of the atlas for obtaining a best overlap with one or more of the plurality of scan images.

The chest wall detector unit 110 is further configured to use a plurality of scan volumes sets generated from the plurality of scans for refining the chest wall model. Each scan volume set of the plurality of scan volumes sets includes a left scan volume, right scan volume, and a center scan volume. In an alternate embodiment, the plurality of scan volumes sets is used to refine the template image. In one embodiment, a machine learning technique may be used to refine the chest wall model or the template image. The machine algorithm may use parameters such as, but not limited to, rib spacing, rib size, and average tissue depth extracted from the plurality of scan volume sets for refining the chest wall model or the template image.

The segmentation unit 112 is communicatively coupled to the chest wall detector unit 110 and configured to provide a plurality of segmented scan images 122. In one embodiment, the segmentation is performed using a graph cut segmentation technique. In another embodiment, the segmentation is performed based on a top-down segmentation technique. In this embodiment, the boundaries of one or more of the plurality of scan images is deformed to provide a best overlap with the template image. In one embodiment, determining the plurality of segmented scan images 122 includes determining a surface representative of a boundary of the chest wall region.

The lesion detector unit 114 is communicatively coupled to the segmentation unit 112 and configured to detect lesions in one or more of the plurality of scan images. In one embodiment, the lesions are detected in a region anterior to the chest wall region. In such an embodiment, the region below the chest wall region in the scan images is removed before applying a lesion detection technique. In another embodiment, the lesions are detected below the chest wall region. In one embodiment, the lesion detector unit 114 determines the lesions based on an automatic lesion detection technique without requiring assistance from a user. In an alternative embodiment, a user assisted segmentation technique may be used to determine the lesions in one or more of the plurality of scan images.

The display unit 116 is communicatively coupled to the lesion detector unit 114 and configured to display the automated breast ultrasound image volumes and provide visualization output 126 to a user, such as a physician. In one embodiment, the ultrasound images are displayed along with chest wall information, ribs information, and the lesion information. In an alternative embodiment, at least one of the chest wall information, ribs information, and the lesion information is displayed along with the ultrasound image. In one embodiment, the physician is provided with an option to view one or more of the plurality of scan images without any additional information. In one embodiment, lesion information above the chest wall is displayed and the lesion information below the chest wall is not displayed, thereby reducing the false positives in the displayed lesions in the ultrasound images.

The memory unit 118 is communicatively coupled to the communication bus 124 and may be accessed by one or more of the chest wall detector unit 110, the segmentation unit 112, the lesion detector unit 114, and the display unit 116. In an exemplary embodiment, the memory unit 118 may include one or more memory modules. The memory unit 118 may be a non-transitory storage medium. For example, the memory may be a dynamic random access memory (DRAM) device, a static random access memory (SRAM) device, flash memory, or other memory devices. In one embodiment, the memory may include a non-volatile memory or similar permanent storage device, media such as a hard disk drive, a floppy disk drive, a compact disc read only memory (CD-ROM) device, a digital versatile disc read only memory (DVD-ROM) device, a digital versatile disc random access memory (DVD-RAM) device, a digital versatile disc rewritable (DVD-RW) device, a flash memory device, or other non-volatile storage devices. In another embodiment, a non-transitory computer readable medium may be encoded with a program composed of instructions to instruct the processor unit 120 to perform functions of the chest wall detector unit 110, the segmentation unit 112, the lesion detector unit 114, and the display unit 116.

The processor unit 120 is communicatively coupled to the memory unit 118 and may include at least one of an arithmetic logic unit, a microprocessor, a general purpose controller, and a processor array to perform the desired computations or run the computer programs. In one embodiment, the processor unit 120 may be configured to aid the chest wall detector unit 110, the segmentation unit 112, the lesion detector unit 114, and the display unit 116 in performing associated tasks. It may be noted that while the embodiment of FIG. 1 depicts the processor unit 120 as a separate unit, in certain embodiments, the chest wall detector unit 110, the segmentation unit 112, the lesion detector unit 114, and the display unit 116 may include a corresponding processor unit.

Figure 2:
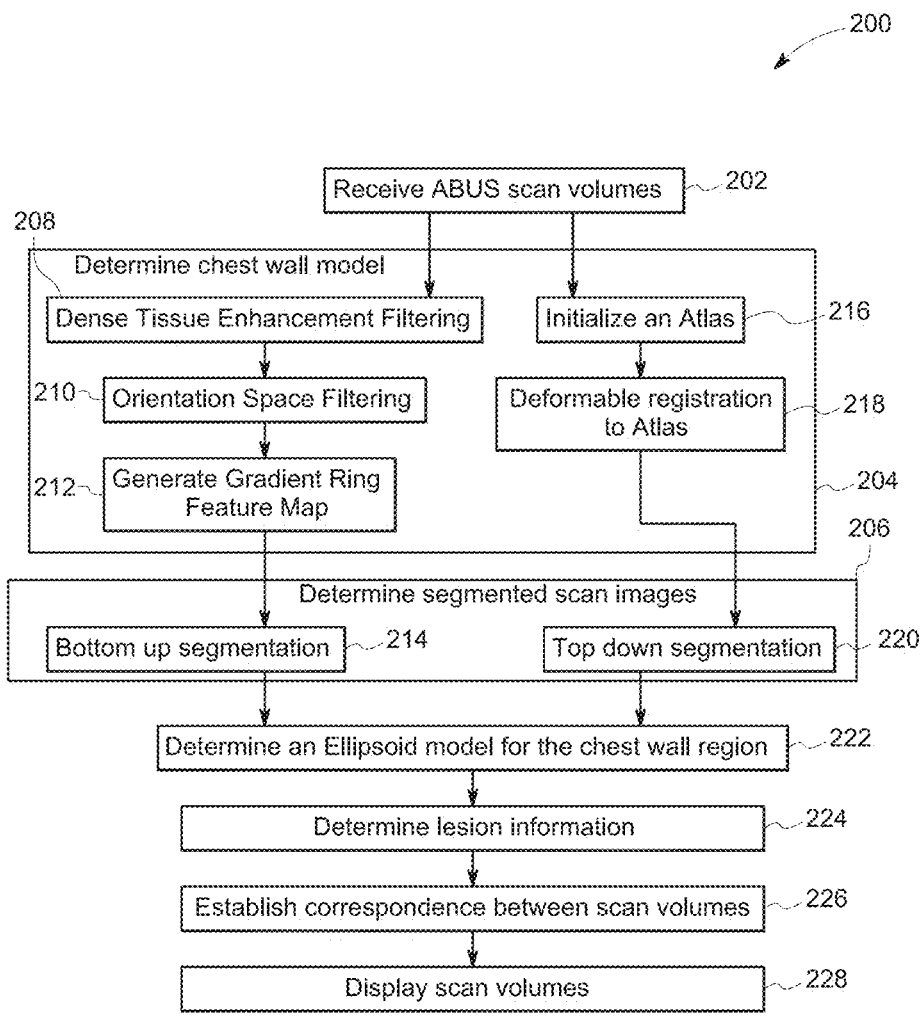
FIG. 2 is a flow chart illustrating a method for visualization of ultrasound volumes, in accordance with aspects of the present specification.

FIG. 2 is a flow chart 200 illustrating a method for visualization of ultrasound volumes, in accordance with aspects of the present specification. At step 202, a plurality of image volumes corresponding to an automated breast ultrasound (ABUS) volume, is received from an ultrasound scanning device. A chest wall model is determined at step 204 based on a plurality of scan images extracted from the plurality of image volumes. Further, at step 206, a segmentation of the chest wall region is performed based on the plurality of scan images and the chest wall model to determine a plurality of segmented scan images. An ellipsoid model is determined for a plurality of points on a surface of the chest wall, at step 222. At step 224, lesion information is determined based on the plurality of segmented scan images. The lesion information includes location and dimensions of one or more lesions detected by a lesion detection technique applied to each of the plurality of segmented scan images. At step 226, the lesions in a left scan volume, a right scan volume, and a center scan volume are aligned to provide view correspondence. Subsequently, at step 228, an assisted reading of the ABUS volume is provided to a physician by displaying at least one of the chest wall information, lesion information, and rib information along with scan images having view correspondence between the left scan, right scan, and center scan volumes.

In one embodiment of step 204, determination of the chest wall model includes processing the plurality of scan images to enhance dense tissues based on a filtering based technique, as illustrated in step 208. In one embodiment, a Hessian filter is used to process the plurality of scan images to generate a plurality of enhanced images. The Hessian filter is a square matrix of second order partial derivatives of a scalar valued function. The Hessian filter is configured to enhance tissues related to local structures of the plurality of image volumes based on relationship of Eigen values of the Hessian matrix. In one embodiment, the local structures include, but are not limited to, a tube-like object, a blob-like object, and a sheet-like object. A threshold is applied to each of the plurality of enhanced images to determine candidate pixels corresponding to the dense tissues. In one embodiment, the threshold is adaptively selected for optimally determining the candidate pixels.

Further, a rough depth map is determined based on the candidate pixels representative of dense tissues in the plurality of scan images. In one embodiment, the depth map is representative of a distance from the skin to pixels on a coronal plane of an image (also referred to as a coronal image). A quadratic surface representative of the chest wall is determined based on the depth map. In one embodiment, the quadratic surface is a cloud of points on the chest wall surface. Further, a coronal image is also determined based on the quadratic surface. In one embodiment, the coronal image is determined by an averaging operation applied to the plurality of scan images with reference to the quadratic surface. As an example, each pixel in the coronal image is determined as an average of pixels of the scan image within a determined distance from the location of the quadratic surface. In one example, the determined distance may be about 5 mm.

At step 210, a rib like region is determined in the plurality of scan images. In addition, at step 210, a rib centerline information is extracted. In one embodiment, an orientation space filtering is used to determine rib like regions. The orientation filter generates an anisotropic response in images having tube like structures. In one embodiment, the orientation filter is used to filter the coronal image to generate an orientation image. In one embodiment, rib centerline information is determined based on the orientation image. The rib centerline information also includes orientation information from noise in the coronal image. In another embodiment, a rib is modelled as a Bezier curve having three control points. For each candidate centerline in the rib centerline information, a cost is determined based on the intensity of the control points associated with the candidate. The candidates having costs lower than a pre-determined centerline threshold are considered as rib centerlines. In another embodiment, a length restriction is also imposed on the Bezier curve to exclude candidate centerlines that are not related to ribs.

In another embodiment, the candidate centerlines which are parallel are considered as rib centerlines.

Further, a gradient ring feature map is generated at step 212. In one embodiment, a first gradient operator is determined along an x-axis and a second gradient operator is determined along a y-axis. A first gradient image is determined by processing a sample image using the first gradient operator. A second gradient image is determined by processing the sample image using the second gradient operator. Further, a feature map is determined based on the first gradient image and the second gradient image. In general, a plurality of gradient images may be determined along a plurality of directions and the feature map is determined based on the plurality of gradient images. In one embodiment, the feature map includes a plurality of feature response values determined based on a direction of gradient corresponding to the rib region. The rib information is determined based on the value of the feature response. It may be noted herein that the feature response includes most salient features and is not affected by speckle noise.

In another embodiment of step 204, an atlas is initialized at step 216. The atlas refers to a chest wall model corresponding to previously acquired breast ultrasound volumes. In one embodiment, an average chest wall model is determined from known chest wall models corresponding to the previously acquired ultrasound volumes. In another embodiment, a pre-determined chest wall model is retrieved from the memory unit. Step 216 is the first step of the two-step registration technique. Further, at step 218, the pre-determined chest wall model is registered to each of the images of the plurality of images. The registration at step 218 is a deformable registration that is used to generate a plurality of registered images. The deformable registration step involves one or more of rotation, translation, and scaling of each of the plurality of images. The deformable registration also includes modifying the boundaries of an image to have a best match with the atlas. Step 218 is the second step of the two-step registration technique.

In one embodiment of the segmentation step 206, a bottom up segmentation technique is used (step 214) to determine the plurality of segmented scan images segmented along the chest wall region based on the chest wall model. Image segmentation refers to partitioning of an image into multiple segments with pixels in each segment sharing common characteristics. In the bottom-up segmentation of step 214, similar smaller portions related to a single object within a scan image are identified. Further, similar portions are combined to form an image segment. In one embodiment of the bottom-up segmentation, a graph cut segmentation is used. In such an embodiment, an image is considered as a graph with pixels corresponding to nodes and a link between each pair of pixels in the image has a weight representative of a similarity between pixels of the pair. A graph having ordered nodes is referred to as a directed graph. By way of example, an s-t graph is a directed graph with a source node s and a sink node t. An s-t cut c(s, t) in a graph is a set of links E such that there is no path from the source s to sink t when E is removed from the graph. The cost of a cut E is the sum of the weights of links in the set E. It is desirable to minimize c(s, t). In particular, it is desirable to determine an s-t cut having a minimal cost c(s, t). The graph cut segmentation technique is equivalent to constructing a graph corresponding to an image such that the minimal cut of this graph segments the image.

In another embodiment of the segmentation step 206, a top-down segmentation technique is performed at step 220 for each of the plurality of scan images obtained from the step 218 to determine the plurality of segmented scan images. In one embodiment, the top-down segmentation technique includes dividing each of the plurality of scan images obtained from the step 218 recursively into smaller portions to segment the image along the pre-determined chest wall model.

At step 222, an ellipsoid model is conformed to the quadratic surface determined at step 208. To that end, first an ellipsoid model template is determined based on an average chest size from biometry data available from offline experimentation and analysis. Alternatively, the ellipsoid model template is determined based on archived ultrasound images. An optimization technique is used to register the ellipsoid model template to the quadratic surface. A cost function representative of a sum of the shortest distances from points on the quadratic surface to the ellipsoid model is used by the optimization technique. In one embodiment, a six degree of freedom is allowed to the points on the quadratic surface. The six degrees of freedom correspond to translations and rotations about three orthogonal axes. The optimization technique provides a transformation of the points to the ellipsoid model. In one embodiment, an inverse of the transformation is used for transferring the ellipsoid model onto the image space. Specifically, the inverse of the transformation is used to determine location and orientation of the ellipsoid model in the image space.

In another embodiment, a point cloud model of the chest wall is determined based on the computed tomography (CT) volumes of the chest. In one embodiment, the point cloud model may be a model template requiring registration and inversion. In another embodiment, the point cloud model may be specific to the subject under consideration.

Further, at step 224, a lesion detection technique is used to determine lesion information in the plurality of scan images. In one embodiment, the lesion detection is performed based on an automated technique. In another embodiment, the lesion detection is performed based on a semi-automatic technique that entails manual intervention. A plurality of techniques involving learning algorithms and classifier models are used for lesion detection in the plurality of scan images extracted from the ultrasound volumes and generation of lesion information.

In one embodiment, at step 226, one of the plurality of ultrasound image volumes is synchronized with the rest of the plurality of ultrasound image volumes. Specifically, a correspondence between the left scan volume, the right scan volume, and the center scan volume is established based on at least one fiducial feature in the plurality of ultrasound image volumes. In one embodiment, a nipple location, identified in one of the steps of 208, 210, 212, may be used as the fiducial feature for establishing image correspondence across the image volumes. In one embodiment, establishing the correspondence includes selecting a first scan volume and a second scan volume different from the first scan volume selected from the left scan volume, the right scan volume, and the center scan volume. A fiducial feature is identified both in the first scan volume and the second scan volume. The correspondence between the first scan volume and the second scan volume is established in two sub steps. In first sub step, the fiducial feature in the first scan volume is registered with the second scan volume using a rigid registration technique. In second sub step, tissue features of the first scan volume are registered with the second scan volume using a deformable registration technique. In some embodiments, at least one of the left scan volume and the right scan volume is combined with the center scan view. In such embodiments, a left scan image from the left scan volume is selected. A right scan image from the right scan volume and a center scan image from the center scan volume corresponding to the left scan image are also selected. Further, an overlap region between one of the left scan images and the right scan image with the center scan image is identified. A combined image is generated by fusing the center scan image with one of the left scan image and the right scan image. In one example of fusing the center scan image with the left scan image, contents of one of the left scan image and the center scan image is retained in the overlapped region. The choice of the image to be retained in the overlapping region is controlled by the user during image display.

In an alternative embodiment, image volumes across imaging modalities may be synchronized at step 226. In particular, a plurality of image volumes corresponds to imaging modalities such as, but not limited to, CT, MRI, and Digital Breast Tomosynthesis (DBT). In one embodiment, at least one of the rib information, lesion information, or chest wall information determined using image volumes corresponding to one imaging modality may be transferred onto the image volumes generated from another imaging modality. An image fiducial feature such as the nipple location may be used to transfer at least one of the lesion information, chest wall information, and rib information across the image volumes obtained from different imaging modalities.

Figure 3:
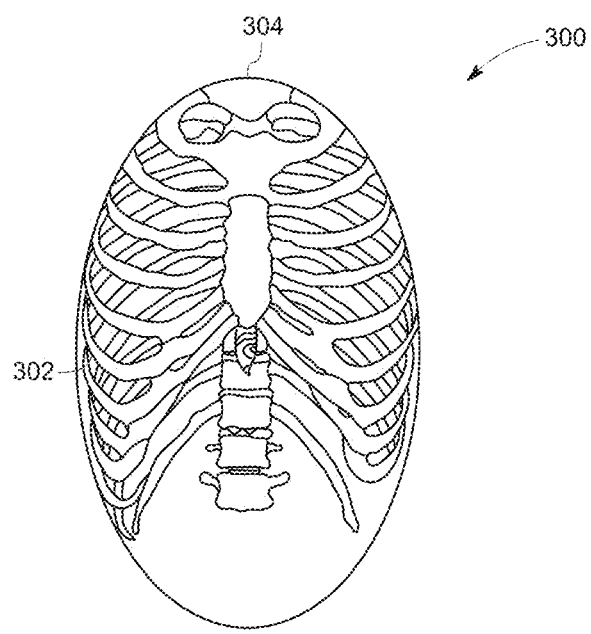
FIG. 3 illustrates front view of an ellipsoid model covering the rib cage, in accordance with aspects of the present specification.

FIG. 3 illustrates a front view 300 of an ellipsoid model covering a rib cage 302, in accordance with one aspect of the present specification. The front view 300 illustrates the rib cage 302 and an ellipse 304 surrounding the rib cage 302. The ellipse 304 is a front view of an ellipsoid model for the chest wall region. Dimensions of the ellipsoid are selected such that a sum of the distances of the rib points from the ellipsoid surface is minimized.

Figure 4:
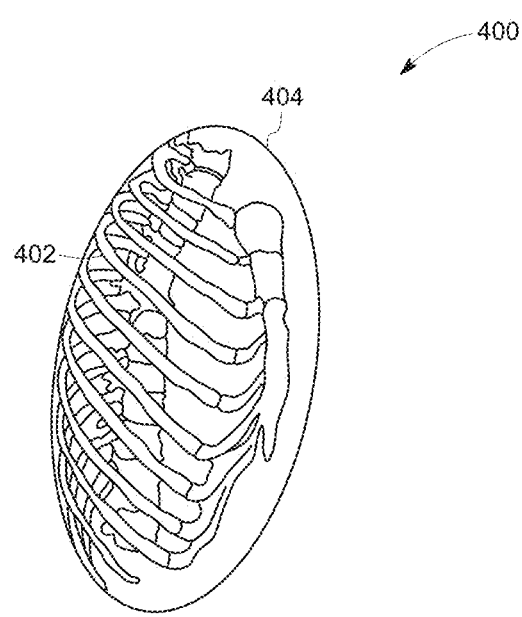
FIG. 4 illustrates a side view of the ellipsoid model covering the rib cage, in accordance with aspects of the present specification.

FIG. 4 illustrates a side view 400 of an ellipsoid model covering a rib cage 402, in accordance with one aspect of the present specification. The side view 400 illustrates the rib cage 402 and an ellipse 404 surrounding the rib cage 402. The ellipse 404 is a side view of an ellipsoid model for modelling the chest wall region. Dimensions of the ellipsoid are selected such that a sum of the distances of the rib points from the ellipsoid surface is minimized.

Figure 5:
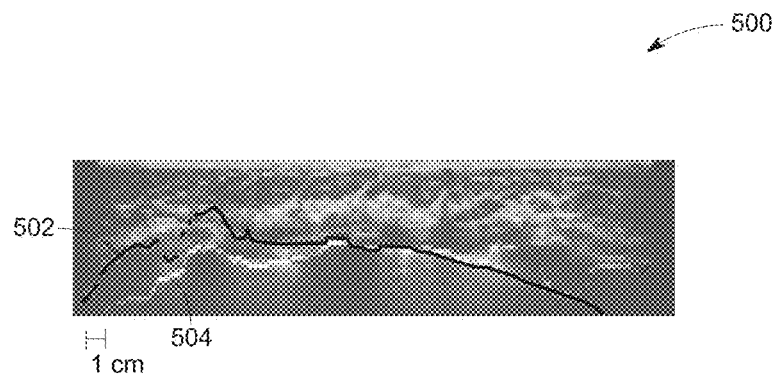
FIG. 5 is a lateral view of an image illustrating effectiveness of a direct registration technique, in accordance with aspects of the present specification.

FIG. 5 is a lateral view of an image 500 illustrating effectiveness of a conventional direct registration technique. The image 500 includes a hull 504 from an atlas and an actual chest wall 502 from an ultrasound image. The image 500 shows registration of the hull 504 to the actual chest wall 502 using the direct registration technique. It may be observed that the registration is poor in the initial portion.

Figure 6:
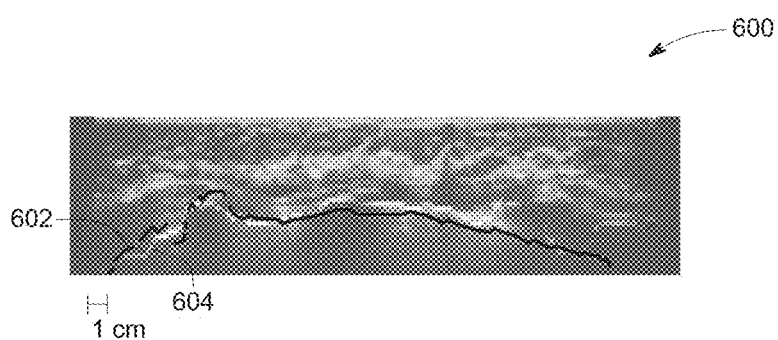
FIG. 6 is a lateral view of an image illustrating effectiveness of a two-step registration technique in accordance with aspects of the present specification.

FIG. 6 is a lateral view of an image 600 illustrating effectiveness of a two-step registration technique in accordance with aspects of present specification. The image 600 includes a hull 604 from an atlas and an actual chest wall 602 from an ultrasound image. The image 600 shows registration of the hull 604 to the actual chest wall 602 using the two-step registration technique. As illustrated, advantageously, the two-step registration technique provides enhanced registration along a plurality of points of the chest wall.

Figure 7:
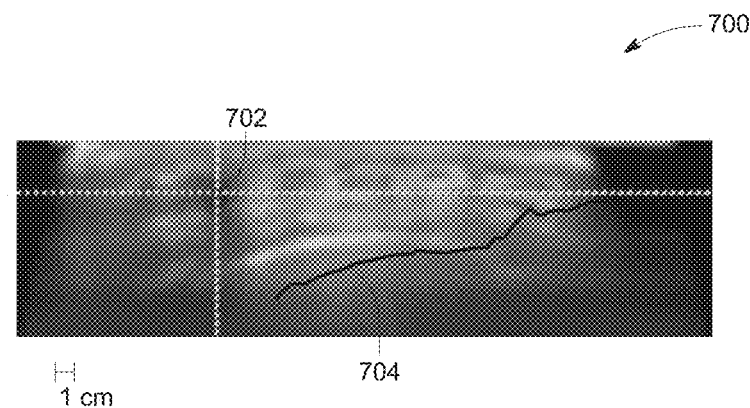
FIG. 7 is an image illustrating a true positive case of lesion detection, in accordance with aspects of present specification.

FIG. 7 is an image 700 illustrating a true positive case of lesion detection, in accordance with aspects of present specification. The image 700 illustrates a lesion at point 702 detected using an automatic lesion detection technique. The image 700 also includes a chest wall boundary 704 identified using a chest wall model. The detected lesion at point 702 lies above the chest wall boundary 704 and is representative of a true positive case.

Figure 8:
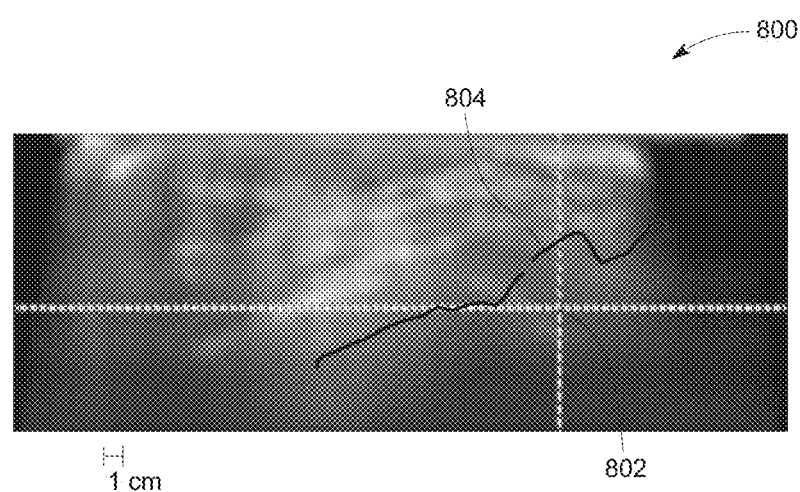
FIG. 8 is an image illustrating a false positive case of lesion detection, in accordance with aspects of the present specification.

FIG. 8 is an image 800 illustrating a false positive case of lesion detection, in accordance with aspects of present specification. The image 800 illustrates a lesion at point 802 detected using an automatic lesion detection technique. The image 800 also includes a chest wall boundary 804 identified using a chest wall model. The detected lesion at point 802 lies below the chest wall boundary 804 and is representative of a false positive case.

Figure 9:
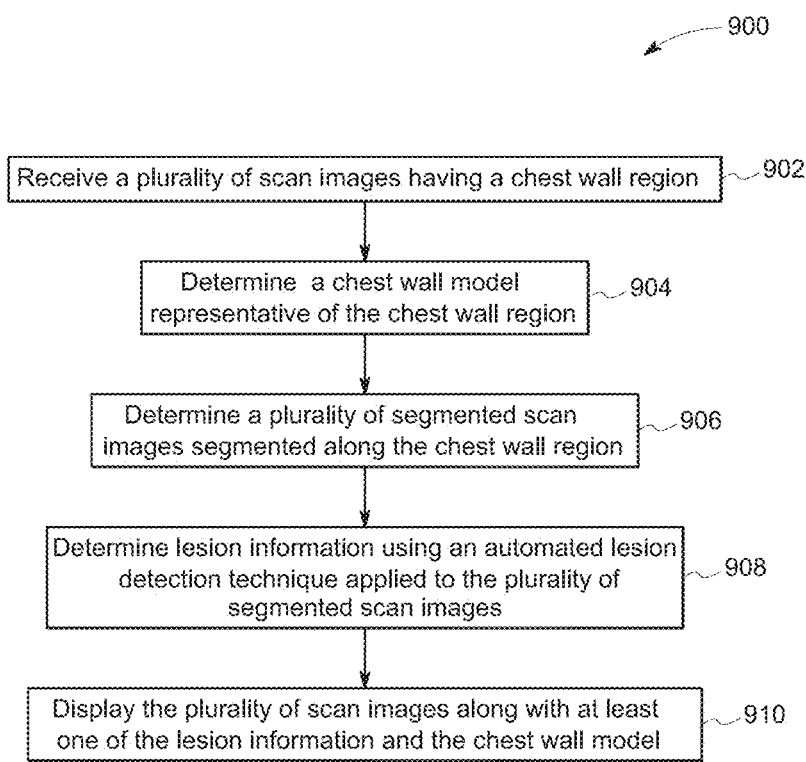
FIG. 9 is a flow chart of a method for visualization of ultrasound volumes in accordance with aspects of the present specification.

FIG. 9 is a flow chart 900 of a method for visualization of ultrasound volumes, in accordance with aspects of the present specification. At step 902, the method includes receiving a plurality of scan images generated from an ultrasound device configured to examine a patient. The plurality of scan images is extracted from one of a left scan volume, a right scan volume, and a center scan volume and includes a chest wall region. The method further includes determining a chest wall model representative of the chest wall region based on the plurality of scan images, as indicated by step 904. In one embodiment, determining the chest wall model includes determining a plurality of points representative of the chest wall region. In another embodiment, determining the chest wall model includes determining an ellipsoid model for the chest wall region. In yet another embodiment, determining the chest wall model also includes determining rib information in the chest wall region. In another embodiment of determining the chest wall, a template image is aligned with each of the plurality of scan images using a deformable registration technique. In one embodiment of determining the rib information, a rib centerline information is determined based on an orientation filtering technique. In another embodiment of determining the rib information, a gradient ring feature map is generated based on the gradient information representative of salient features of rib cage in the chest wall region.

At step 906, the method also includes determining a plurality of segmented scan images segmented along the chest wall region based on the chest wall model. In one embodiment, a bottom-up segmentation technique is used for generating the plurality of segmented scan images. In another embodiment, each of the plurality of scan images is aligned with the template image using a top-down segmentation technique. At step 908, the method includes determining lesion information using an automated lesion detection technique applied to the plurality of segmented scan images. Further, at step 910, the method includes displaying the plurality of scan images along with at least one of the lesion information and the chest wall model. In one embodiment, displaying includes establishing correspondence between at least two of the left scan volume, the right scan volume, and the center scan volume using a fiducial feature in the plurality of scan images. In another embodiment, displaying includes transferring at least one of the visualizing lesion information and the chest wall information corresponding to a plurality of scan images obtained from another imaging modality using a fiducial feature.

Embodiments of systems and methods disclosed herein help in reducing false positives during automatic lesion detection in ABUS volumes. Further, disclosed technique provides flexibility of selecting one or more computer aided visualization options to enhance the confidence of both expert and novice users during assisted reading of ABUS volumes.

It is to be understood that not necessarily all such objects or advantages described above may be achieved in accordance with any particular embodiment. Thus, for example, those skilled in the art will recognize that the systems and techniques described herein may be embodied or carried out in a manner that achieves or improves one advantage or group of advantages as taught herein without necessarily achieving other objects or advantages as may be taught or suggested herein.

While the technology has been described in detail in connection with only a limited number of embodiments, it should be readily understood that the specification is not limited to such disclosed embodiments. Rather, the technology can be modified to incorporate any number of variations, alterations, substitutions or equivalent arrangements not heretofore described, but which are commensurate with the spirit and scope of the claims. Additionally, while various embodiments of the technology have been described, it is to be understood that aspects of the specification may include only some of the described embodiments. Accordingly, the specification is not to be seen as limited by the foregoing description, but is only limited by the scope of the appended claims.

The invention claimed is:

1. A method, comprising:
   receiving an automated breast ultrasound (ABUS) volume acquired with an ultrasound imaging system;
   extracting a plurality of scan images from the ABUS volume, wherein the plurality of scan images comprise a chest wall region;
   determining a chest wall model representative of the chest wall region based on the plurality of scan images, wherein said determining the chest wall model comprises using a machine learning technique to refine the chest wall model; and
   determining a plurality of segmented scan images segmented along the chest wall region based on the chest wall model, wherein the plurality of segmented scan images include a region anterior to the chest wall region.

2. The method of claim 1, wherein determining the chest wall model comprises using a two-step registration technique comprising a first step and a second step, wherein the first step comprises initializing an atlas for registration with the plurality of scan images, and the second step comprises using a deformable registration technique to align the atlas with one or more of the plurality of scan images.

3. The method of claim 1, wherein determining the chest wall model comprises determining an ellipsoid model for the chest wall region.

4. The method of claim 1, wherein determining the chest wall model comprises determining rib information in the chest wall region.

5. The method of claim 1, wherein determining the chest wall model comprises determining a rib centerline information.

6. The method of claim 1, wherein determining the chest wall model comprises generating a template image representative of the chest wall model.

7. The method of claim 6, further comprising matching the template image to the plurality of scan images based on a deformable registration technique.

8. The method of claim 1, wherein determining the plurality of segmented scan images comprises determining a surface representative of a boundary of the chest wall region.

9. The method of claim 1, wherein determining the plurality of segmented scan images is based on a bottom-up segmentation technique or a top-down segmentation technique.

10. The method of claim 1, wherein the machine learning technique uses one or more parameters extracted from a plurality of scan volume sets for refining the chest wall model.

11. The method of claim 1, further comprising:
    determining lesion information using an automated lesion detection technique applied to the plurality of segmented scan images, wherein the lesion information includes a location and a dimension for each of one or more lesions detected using the automated lesion detection technique; and
    displaying the plurality of scan images along with the lesion information.

12. The method of claim 11, further comprising displaying the chest wall model at the same time as said displaying the plurality of scan images along with the lesion information.

13. The method of claim 11, wherein determining the chest wall model comprises determining an ellipsoid model for the chest wall region.

14. The method of claim 1, further comprising displaying the plurality of scan images along with chest wall information.

15. A system, comprising:
    an ultrasound scanning device configured to generate an automated breast ultrasound (ABUS) volume;
    a processor unit communicatively coupled to the ultrasound scanning device and configured to extract a plurality of scan images from the ABUS volume, wherein the plurality of scan images comprise a chest wall region;
    a chest wall detector unit communicatively coupled to the imaging device and configured to generate a chest wall model based on the plurality of scan images, wherein the chest wall detector unit is configured to generate the chest wall model using a machine learning technique to refine the chest wall model; and
    a segmentation unit communicatively coupled to the chest wall detector unit and configured to segment the plurality of scan images along a boundary of the chest wall to determine a plurality of segmented scan images, wherein the plurality of segmented scan images include a region anterior to the chest wall region.

16. The system of claim 15, wherein the chest wall detector unit is configured to determine an ellipsoid model for the chest wall region.

17. The system of claim 15, wherein the chest wall detector unit is configured to determine rib information in the chest wall region.

18. The system of claim 15, wherein the chest wall detector unit is configured to determine a rib centerline information.

19. The system of claim 15, wherein the chest wall detector unit is configured to generate a template image representative of a chest wall model.

20. The system of claim 19, wherein the chest wall detector unit is configured to match the template image to the plurality of scan images based on a deformable registration technique.

21. The system of claim 15, wherein the segmentation unit is configured to determine a surface representative of boundary of the chest wall region.

22. The system of claim 15, wherein the chest wall detector unit is configured to generate the chest wall model using a two-step registration technique comprising a first step and a second step, the first step comprising initializing an atlas for registration with the plurality of scan images, and the second step comprising using a deformable registration technique to align the atlas with one or more of the plurality of scan images.

23. The system of claim 15, wherein the machine learning technique uses one or more parameters extracted from a plurality of scan volume sets for refining the chest wall model.

24. The system of claim 15, further comprising:
- a lesion detector unit communicatively coupled to the segmentation unit and configured to generate lesion information using an automated lesion detection technique, wherein the lesion information includes a location and a dimension for each of one or more lesions detected using the automated lesion detection technique; and
- a display unit communicatively coupled to the lesion detector unit and configured to display the plurality of scan images along with the lesion information.

25. The system of claim 24, wherein the display unit is configured to display the chest wall model while displaying the plurality of scan images along with the lesion information.

26. The system of claim 24, wherein the chest wall detector unit is configured to determine an ellipsoid model for the chest wall region.

* * * * *